US009207157B2

United States Patent
Frelich et al.

(10) Patent No.: US 9,207,157 B2
(45) Date of Patent: Dec. 8, 2015

(54) SYSTEM AND METHOD FOR DETERMINING A STATE OF COMPACTION

(71) Applicant: Caterpillar Paving Products Inc., Brooklyn Park, MN (US)

(72) Inventors: Thomas J. Frelich, Albertville, MN (US); Kyle Hendricks, St. Francis, MN (US); Robert K. Iverson, Maple Grove, MN (US); Craig R. Fausch, Nowthen, MN (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 44 days.

(21) Appl. No.: 14/215,513

(22) Filed: Mar. 17, 2014

(65) Prior Publication Data

US 2015/0260626 A1 Sep. 17, 2015

(51) Int. Cl.
*E01C 19/28* (2006.01)
*E01C 19/23* (2006.01)
*G01N 9/00* (2006.01)
*G01P 3/00* (2006.01)
*G01C 9/00* (2006.01)

(52) U.S. Cl.
CPC ............... *G01N 9/002* (2013.01); *E01C 19/23* (2013.01); *E01C 19/28* (2013.01); *E01C 19/286* (2013.01); *E01C 19/288* (2013.01); *G01C 9/00* (2013.01); *G01P 3/00* (2013.01)

(58) Field of Classification Search
CPC ..... E01C 19/006; E01C 19/26; E01C 19/288; E01C 19/28; E01C 19/23; E01C 19/286; E02D 1/022; E02D 3/026
See application file for complete search history.

(56) References Cited

U.S. PATENT DOCUMENTS

| 3,909,147 | A | 9/1975 | Takata | |
|---|---|---|---|---|
| 4,348,901 | A | 9/1982 | Vural et al. | |
| 5,915,492 | A | 6/1999 | Yates et al. | |
| 5,942,679 | A | 8/1999 | Sandstrom | |
| 6,188,942 | B1 | 2/2001 | Corcoran et al. | |
| 7,483,808 | B2 * | 1/2009 | Greiner et al. | ............... 702/166 |
| 7,623,951 | B2 | 11/2009 | Congdon et al. | |
| 7,731,450 | B2 | 6/2010 | Congdon et al. | |
| 7,919,945 | B2 | 4/2011 | Houston et al. | |
| 8,190,338 | B2 | 5/2012 | Commuri | |
| 8,332,105 | B2 | 12/2012 | Laux | |
| 8,639,420 | B2 | 1/2014 | Corcoran et al. | |
| 2003/0047003 | A1 * | 3/2003 | Miyamoto et al. | ............... 73/660 |
| 2005/0183512 | A1 * | 8/2005 | Corcoran | ....................... 73/818 |

(Continued)

OTHER PUBLICATIONS

Caterpillar Inc., "Machine Drive Power: Cat Compaction Control," 8 pp., 2013.

*Primary Examiner* — Abigail A Risic
(74) *Attorney, Agent, or Firm* — Leydig, Voit & Mayer, Ltd.

(57) ABSTRACT

A system for determining a state of compaction of a work material includes a roller having a vibration system. A controller is configured to determine the speed of the machine, determine an inclination of the machine, and determine an inclination power change based upon the inclination and the speed of the machine. The controller is also configured to determine the gross power loss resulting from the compaction operation, determine a vibration compensation factor based upon vibration characteristics of the vibration system, and determine the state of compaction of the work material based upon the inclination power change, the power loss, and the vibration compensation factor.

14 Claims, 4 Drawing Sheets

(56) References Cited

U.S. PATENT DOCUMENTS

| | | | |
|---|---|---|---|
| 2007/0150147 A1* | 6/2007 | Rasmussen et al. | 701/50 |
| 2007/0239336 A1* | 10/2007 | Congdon et al. | 701/50 |
| 2007/0239338 A1* | 10/2007 | Potts et al. | 701/50 |
| 2009/0143952 A1* | 6/2009 | Chisholm et al. | 701/99 |
| 2010/0087992 A1* | 4/2010 | Glee | 701/50 |
| 2014/0348587 A1* | 11/2014 | Corcoran et al. | 404/84.05 |
| 2015/0211199 A1* | 7/2015 | Corcoran et al. | 404/84.05 |

\* cited by examiner

SYSTEM AND METHOD FOR DETERMINING A STATE OF COMPACTION

TECHNICAL FIELD

This disclosure relates generally to machines that compact material, and more particularly, to a system and method for determining a state of compaction of a work material at a work site.

BACKGROUND

Compacting machines or compactors are commonly used to compact work materials (such as soil, gravel, asphalt) to a desired density while constructing buildings, highways, parking lots, and other structures. In addition, compactors are often used to compact recently moved and/or relatively soft materials at mining sites and landfills. The process often requires a plurality of passes over the work material to reach the desired density.

Determining whether the desired level of compaction has been reached is often estimated in a variety of manners. In some instances, the compaction may be approximated by a state of compaction system that measures the amount of power required to move the compactor along the surface of a work site. The state of compaction system may determine a state of compaction relative to an absolute scale or a maximum amount of compaction. However, utilizing a vibration system with the compactor may affect the results of the state of compaction system.

U.S. Pat. No. 6,188,942 discloses a method and apparatus for use with a compactor to determine the compaction performance of a material. The compaction performance may be determined as a function of the compactive energy or as a function of the propelling power of the compactor.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

In a one aspect, a system for determining a state of compaction of a work material during a compaction operation includes a roller associated with a machine. The roller includes a vibration system and is configured to engage and compact the work material. The system further includes a speed sensor associated with the machine for generating speed signals indicative of the speed of the machine, a pitch angle sensor associated with the machine for generating inclination signals indicative of the inclination of the machine, and a power loss sensor associated with the machine for generating signals indicative of the power loss of the machine. A controller is configured to receive the speed signals from the speed sensor indicative of the speed of the machine, determine the speed of the machine based upon the speed signals, and receive the inclinations signals from the pitch angle sensor indicative of the inclination of the machine. The controller is further configured to determine the inclination of the machine based upon the inclination signals, determine an inclination power change based upon the inclination and the speed of the machine, and receive signals from the power loss sensor indicative of the power loss of the machine. The controller is also configured to determine the power loss of the machine based upon the signals, determine a vibration compensation factor based upon vibration characteristics of the vibration system, and determine the state of compaction of the work material based upon the inclination power change, the power loss, and the vibration compensation factor.

In another aspect, a controller-implemented method for determining a state of compaction of a work material during a compaction operation includes determining the speed of the machine based upon the speed signals from a speed sensor, determining an inclination power change based upon the inclination of the machine and the speed of the machine, and determining the power loss of the machine based upon the signals from a power loss sensor. The method further includes determining a vibration compensation factor based upon vibration characteristics of the vibration system and determining the state of compaction of the work material based upon the inclination power change, the power loss, and the vibration compensation factor.

In still another aspect, a machine includes a prime mover and a roller operatively connected to the prime mover. The roller includes a vibration system and is configured to engage and compact the work material. A speed sensor is associated with the machine for generating speed signals indicative of the speed of the machine, a pitch angle sensor is associated with the machine for generating inclination signals indicative of the inclination of the machine, and a power loss sensor is associated with the machine for generating signals indicative of the power loss of the machine A controller is configured to store friction loss characteristics of the machine, receive the speed signals from the speed sensor indicative of the speed of the machine, and determine the speed of the machine based upon the speed signals. The controller is further configured to determine a machine friction loss based upon the friction loss characteristics and the speed of the machine, receive the inclinations signals from the pitch angle sensor indicative of the inclination of the machine, determine the inclination of the machine based upon the inclination signals, and determine an inclination power change based upon the inclination and the speed of the machine. The controller is also configured to receive signals from the power loss sensor indicative of the power loss of the machine, determine the power loss of the machine based upon the signals, and determine a vibration compensation factor based upon vibration characteristics of the vibration system.

DETAILED DESCRIPTION

Figure 1:
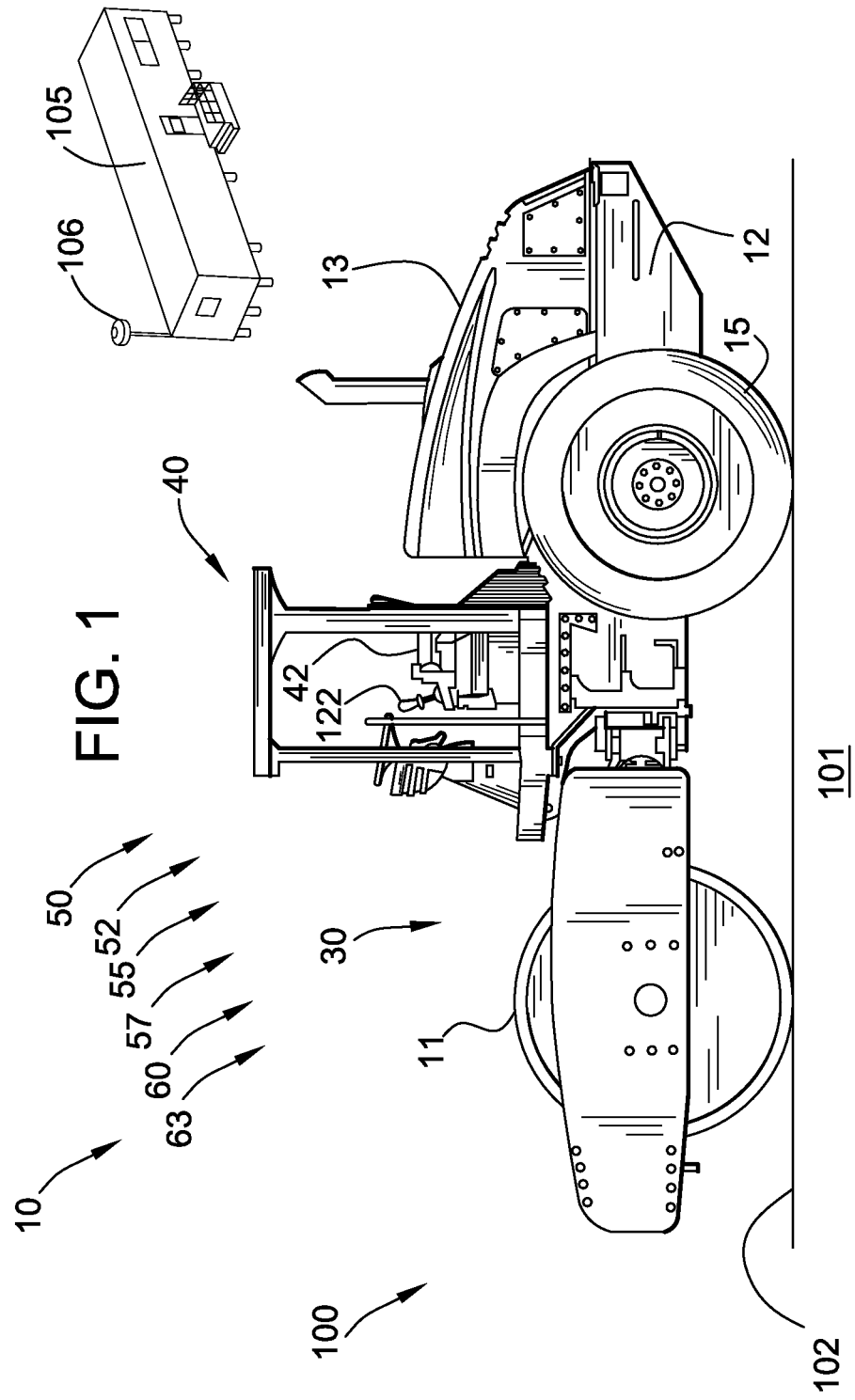
FIG. 1 illustrates a diagrammatic view of a machine in accordance with the disclosure.

FIG. 1 depicts a diagrammatic illustration of a machine 10 such as a self-propelled single drum compactor with a single cylindrical drum or roller 11 for compacting a work material 101 at work site 100. The machine 10 includes a frame 12 and a prime mover such as an engine 13. Engine 13 is a part of a drive system 14 (FIG. 2) that propels the machine 10 as desired. The systems and methods of this disclosure may be used with any machine propulsion and drivetrain mechanisms applicable in the art including hydrostatic, electric, or mechanical drives. The drive system 14 may operate to drive roller 11 and/or one or more deflectable tires 15. In other embodiments, other types of work material engaging members may be used such as replacing the deflectable tires 15 with another roller.

Figure 2:
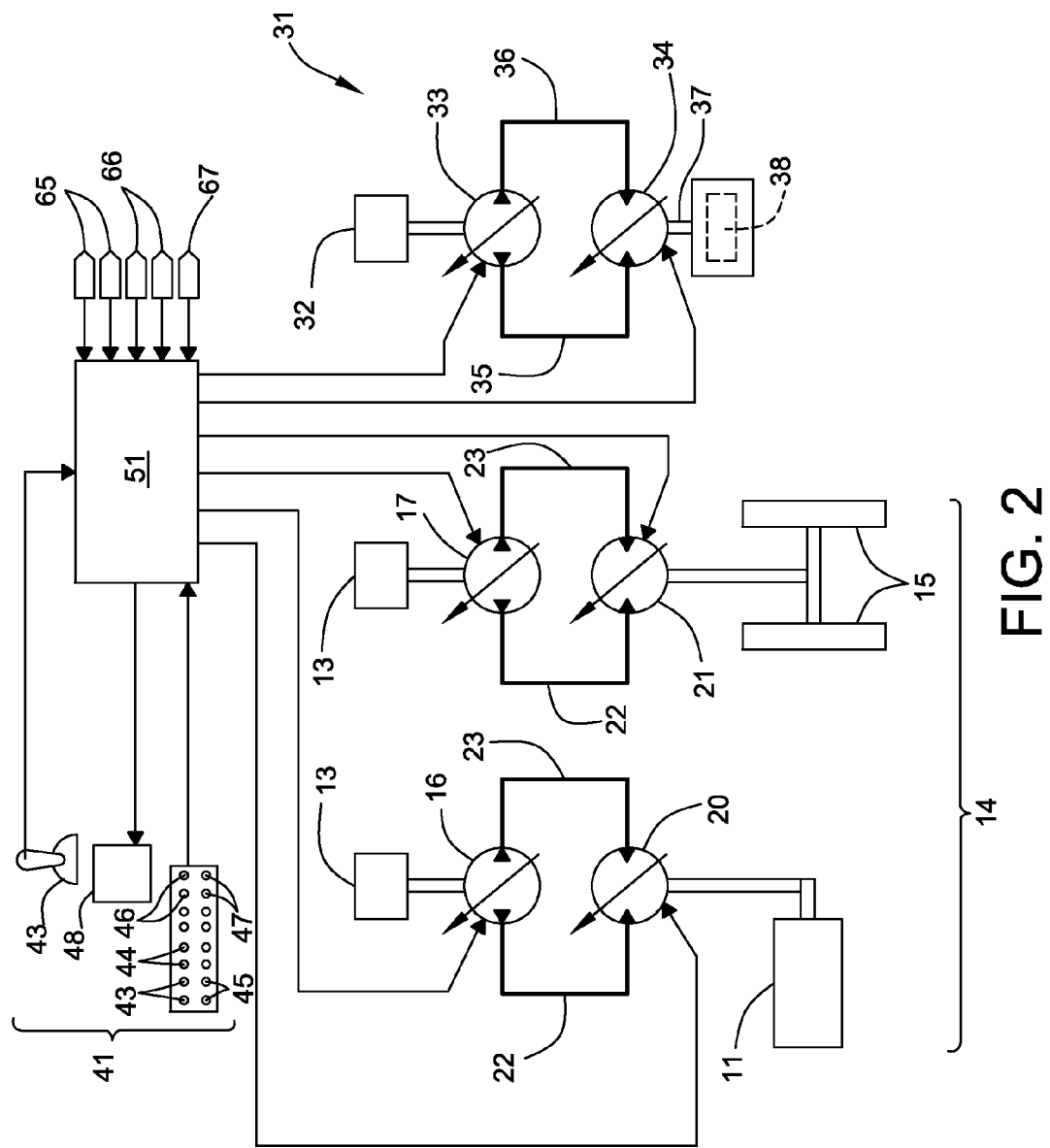
FIG. 2 illustrates a schematic view of an exemplary drive system, vibration system, and an operator station for use with the machine of FIG. 1.

In one embodiment depicted in FIG. 2, drive system 14 may be a hydrostatic system in which engine 13 is operatively connected to first pump 16 and second pump 17. Each of the first pump 16 and the second pump 17 may be operatively hydraulically connected to power first motor 20 and second motor 21, respectively, via a first hydraulic line 22 and a second hydraulic line 23. First motor 20 may be driven by pressurized hydraulic fluid from first pump 16 to rotate roller 11 and second motor 21 may be driven by pressurized hydraulic fluid from second pump 17 to rotate deflectable tires 15.

Each of first pump 16 and second pump 17 may be a variable displacement pump with the displacement controlled by controller 51. In one embodiment, signals from controller 51 may be used to control or adjust the displacement of the first pump 16 and second pump 17. First pump 16 and second pump 17 may each direct pressurized hydraulic fluid to and from their respective motors in two different directions to operate the motors in forward and reverse directions. First pump 16 and second pump 17 may each include a stroke-adjusting mechanism, for example a swashplate, the position of which is hydro- or electro-mechanically adjusted to vary the output (e.g., a discharge pressure or rate) of the pump. The displacement of each of the first pump 16 and the second pump 17 may be adjusted from a zero displacement position, at which substantially no fluid is discharged from the pump, to a maximum displacement position, at which fluid is discharged from the pump at a maximum rate. The displacement of each of the first pump 16 and the second pump 17 may be adjusted so the flow is either into its first hydraulic line 22 or its second hydraulic line 23 so that the pump may drive its respective motor in either forward and reverse directions, depending on the direction of fluid flow. Each of the first pump 16 and the second pump 17 may be operatively connected to engine 13 of machine 10 by, for example, a shaft 24, a belt, or in any other suitable manner.

Each of first motor 20 and second motor 21 may be driven to rotate by a fluid pressure differential generated by its respective pump and supplied through first hydraulic line 22 and second hydraulic line 23. More specifically, each motor may include first and second chambers (not shown) located on opposite sides of a pumping mechanism such as an impeller, plunger, or series of pistons (not shown). When the first chamber is filled with pressurized fluid from the pump via first hydraulic line 22 and the second chamber is drained of fluid returning to the pump via second hydraulic line 23, the pumping mechanism is urged to move or rotate in a first direction (e.g., in a forward traveling direction). Conversely, when the first chamber is drained of fluid and the second chamber is filled with pressurized fluid, the pumping mechanism is urged to move or rotate in an opposite direction (e.g., in a rearward traveling direction). The flow rate of fluid into and out of the first and second chambers may determine an output velocity of the motor, while a pressure differential across the pumping mechanism may determine an output torque.

Each of first motor 20 and second motor 21 may be a variable displacement motor with the displacement controlled by controller 51. In that configuration, the motor has an infinite number of configurations or displacements. In another embodiment, each of first motor 20 and second motor 21 may be a fixed and/or a multi-speed motor. In that configuration, the motor has a finite number of configurations or displacements (e. g., two) between which the motor may be shifted. The motor may thus operate as a fixed displacement motor with a plurality of distinct displacements.

Machine 10 may also include a vibratory or vibration system indicated generally at 30 (FIG. 1) associated with roller 11 to impart a compacting force onto the work material 101. More specifically, in addition to the weight of roller 11 and machine 10 being applied to the work material 101 to apply compressive forces, the vibration system 30 within roller 11 may operate to apply additional forces to the work material. As used herein, vibration system 30 includes any type of system that imparts vibrations, oscillations, or other repeating forces through roller 11 onto work material 101.

Vibration system 30 may take any desired form. In one embodiment depicted in FIG. 2, the vibration system 30 may utilize a hydraulic drive system 31 including a vibration system engine 32, distinct from engine 13, that is operatively connected to vibration system pump 33. The vibration system pump 33 may be operatively connected to power a vibration system motor 34 via a first vibration system hydraulic line 35 and a second vibration system hydraulic line 36. Vibration system motor 34 may drive one or more rotatable vibration system shafts 37 that rotate one or more eccentrically mounted masses 38 within roller 11 to create a vibrating or oscillatory force within the roller 11 that is imparted to the work material 101.

Other manners of configuring the vibration system 30 are contemplated. For example, if desired, vibration system engine 31 may be omitted and vibration system pump 33 may be operatively connected to engine 13. Further, in other embodiments, the masses may be moved by mechanical, electrical, or electro-magnetic systems. In addition, in some embodiments, the masses may be moved linearly rather than eccentrically as part of a rotational system.

Machine 10 may include an operator station 40 from which an operator may control the machine 10. Operator station 40 may include an operator interface 41 (FIG. 2) proximate an operator seat 42 through which the operator may issue commands to control propulsion and steering systems of the machine 10 as well as operate other systems and implements associated with the machine. Operator interface 41 may include a plurality of input devices including a throttle input 43, a transmission input 44, a speed input 45, a vibration frequency input 46, and a vibration amplitude input 47. Each input device may take the form of a joystick, pedal, a push-button, a knob, a switch, or another device. The operator may manipulate the input device to affect corresponding operations of machine 10. Operator interface 41 may further include a display 48 on which various types of information useful or necessary for the operation of the machine 10 may be displayed. Additional operator input devices and displays may be included, if desired.

Throttle input 43 is depicted as a joystick that is tiltable through a range from a neutral position to one or more maximum displacement positions to generate one or more corresponding throttle input signals that are indicative of a desired percentage of the maximum speed of the machine in particular directions. Throttle input 43 may be tiltable from the neutral position to a maximum displaced position in a first direction (e.g. forward) to generate a corresponding first throttle signal. Likewise, throttle input 43 may be tiltable from the neutral position to a maximum displaced position in a second direction (e.g., rearward) to generate a second throttle signal. Values of the first and second throttle signals may correspond to desired percentages of the maximum speed setting for the machine in the forward and reverse directions of travel of the machine, respectively. In other words, the displacement of the throttle input 43 may be directly proportional to the percentage of the maximum speed of the machine based upon a setting or command from an operator or other personnel or as otherwise set within the machine 10.

Transmission input 44 and speed input 45 may be used by an operator to select different modes of operation. More specifically, transmission input 44 may be a plurality of push buttons that, when pressed by the operator of machine 10, select one of any number of available transmission control settings (i.e., virtual gears or portions of a continuous range of transmission speed-to-torque ratios). For example, the operator may press a first of the push buttons to select a first gear, in which drive system 14 may operate within a highest torque output range and a corresponding lowest travel speed range. Likewise, the operator may press a second of the push buttons to select a second or higher gear, in which drive system 14 may operate with a lower torque output range and a corresponding higher travel speed range.

Speed input 45 may also be a plurality of push buttons that, when pressed by the operator of machine 10, select one of any number of maximum allowable speeds or available machine travel speed limits that correspond to the maximum displaced position of throttle input 43.

Vibration frequency input 46 and vibration amplitude input 47 may form a portion of vibration system 30. Vibration frequency input 46 may be a plurality of push buttons for establishing the frequency of vibrations imparted on the work material 101 by roller 11. More specifically, the vibration frequency input 46 may be used to set the rate at which the masses 38 move and thus the frequency at which the roller 11 impacts the work surface 102.

Vibration amplitude input 47 may also be a plurality of push buttons for establishing the amplitude of vibrations imparted on the work material 101 by roller 11. More specifically, the vibration amplitude input 47 may be used to set the stroke of the masses 38 and thus establish the force of impact between the roller 11 and the work surface 102.

Vibration system 30 may permit an infinite number of adjustments to both the vibration frequency and vibration amplitude or may have a predetermined number of pre-set values for either or both of the vibration frequency and the vibration amplitude. In one example, the vibration frequency may be set to low, medium, or high depending on the characteristics of the work material 101 upon which machine 10 is operating. In addition, the vibration amplitude may be set to low, medium, or high depending on the characteristics of the work material 101. In other instances, the vibration frequency and/or amplitude may be set to specific values based upon the characteristics of the work material 101.

Machine 10 may include a control system 50 as shown generally by an arrow in FIG. 1 indicating association with the machine 10. The control system 50 may include an electronic control module or controller 51, various input devices to control the machine 10, and a plurality of sensors associated with the machine 10 that provide data and input signals representative of various operating parameters of the machine 10. The term "sensor" is meant to be used in its broadest sense to include one or more sensors and related components that may be associated with the machine 10 and that may cooperate to sense various functions, operations, and operating characteristics of the machine.

The controller 51 may be an electronic controller that operates in a logical fashion to perform operations, execute control algorithms, store and retrieve data and other desired operations. The controller 51 may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the controller 51 such as power supply circuitry, signal conditioning circuitry, driver circuitry, and other types of circuitry.

The controller 51 may be a single controller or may include more than one controller disposed to control various functions and/or features of the machine 10. The term "controller" is meant to be used in its broadest sense to include one or more controllers and/or microprocessors that may be associated with the machine 10 and that may cooperate in controlling various functions and operations of the machine. The functionality of the controller 51 may be implemented in hardware and/or software without regard to the functionality. The controller 51 may rely on one or more data maps relating to the operating conditions of the machine 10 that may be stored in the memory of controller. Each of these data maps may include a collection of data in the form of tables, graphs, and/or equations.

The control system 50 may be located on the machine 10 and may also include components located remotely from the machine such as at a command center 105. The functionality of control system 50 may be distributed so that certain functions are performed at machine 10 and other functions are performed remotely. In such case, the control system 50 may include a communications system such as wireless network system 106 for transmitting signals between the machine 10 and a system located remote from the machine.

A position sensing system 55, as shown generally by an arrow in FIG. 1 indicating association with the machine 10, may include a position sensor 56 to sense a position of the machine relative to the work site 100. The position sensor 56 may include a plurality of individual sensors that cooperate to provide signals to controller 51 to indicate the position of the machine 10. In one example, the position sensor 56 may include one or more sensors that interact with a positioning system such as a global navigation satellite system or a global positioning system to operate as a position sensor. The controller 51 may determine the position of the machine 10 within work site 100 as well as the orientation of the machine such as its heading, pitch and roll. In other examples, the position sensor 56 may be an odometer or another wheel rotation sensing sensor, a perception based system, or may use other systems such as lasers, sonar, or radar to determine the position of the machine 10.

Machine 10 may also include a drive speed sensing system 57, as shown generally by an arrow in FIG. 1 indicating association with the machine 10. The drive speed sensing system 57 may include a speed sensor 58 for generating speed signals indicative of the speed of the machine 10. Controller 51 may utilize the speed signals to determine the speed of the machine 10 relative to work surface 102. In one example, the speed sensor 58 may be a magnetic sensor associated with second motor 21, which is used to drive the deflectable tires 15. In another embodiment, controller 51 may utilize data from the position sensing system 55 to determine the speed of the machine.

Machine 10 may also include an inclination sensing system 60, as shown generally by an arrow in FIG. 1 indicating association with the machine 10, for determining the inclination or pitch angle of the machine relative to a level ground reference (i.e., perpendicular to the direction of gravity). The inclination sensing system may include an inclination or pitch angle sensor 61 for generating inclination signals that are used by controller 51 to determine the inclination of machine 10. In some embodiments, the inclination sensing system 60 may use a pitch rate sensor 62 in addition to or instead of the pitch angle sensor 61 to determine the pitch angle of the machine 10.

Machine 10 may also include various sensors associated with each of the drive system 14 and the vibration system 30. For example, the machine 10 may include a power loss measurement system 63 for determining the amount of power lost or used during a compaction operation of the machine. The power loss measurement system 63 may include a power loss sensor 64 for generating signals indicative of power loss of the machine during a compaction operation. In one embodiment, the power loss sensor 64 may embody motor hydraulic sensors 65 (FIG. 2) to measure the difference between the hydraulic pressure within the first hydraulic line 22 and second hydraulic line 23 at the input and output of each of the first motor 20 and the second motor 21. The amount of power used to compact the work material 101 may be calculated based upon the change in hydraulic pressure between the input and the output of each of the first motor 20 and the second motor 21.

In another embodiment, the power loss sensor 64 may use pump hydraulic sensors 66 (FIG. 2) to measure the difference between the hydraulic pressure within the first hydraulic line 22 and second hydraulic line 23 at the input and output of each of the first pump 16 and the second pump 17. The amount of power used to compact the work material 101 may be calculated based upon the change in hydraulic pressure between the input and the output of each of the first pump 16 and the second pump 17 together with an estimate of line losses that occur as a result of hydraulic fluid being pumped through or along the first hydraulic line 22 and second hydraulic line 23 between each pump and its respective motor.

In still another embodiment, the drive system 14 may include a mechanical drive with a torque converter (not shown). In such case, the power loss sensor 64 may include sensors that are used to determine the input speed of the torque converter (or the output speed of engine 13) and the output speed of the torque converter. The amount of power used to compact the work material 101 may be calculated based upon the change in speed between the input and the output of the torque converter.

Vibration system 30 may include a hydraulic drive system 31 to impart additional force to the work material 101 as described above. Hydraulic sensor 67 may be operatively associated with the first vibration system hydraulic line 35 or the second vibration system hydraulic line 36 to determine the pressure within or of the relevant hydraulic line. As the work material 101 is compacted and increases in stiffness, the pressure within the hydraulic lines will increase even as the settings of the vibration system engine 32, vibration system pump 33, and the vibration system motor 34 remain the same.

Control system 50 may include a state of compaction system 52 for determining the level or state of compaction of work material 101 as machine 10 moves over the work surface 102. As the machine 10 moves along the work surface 102, power is used to compact the work material 101, to move the machine, and to overcome friction losses of the machine, and power is gained or lost depending on whether the machine is traveling down or up a grade. The state of compaction system 52 generally operates based upon the concept that less power is required to move a machine across a harder or more compacted work material 101 as compared to a softer or less compacted work material. By determining the actual drive power ($P_{Actual}$) used by the machine 10 as it moves along the work surface 102 and compacts the work material 101, a relative state of compaction of the work material may be determined. The actual drive power ($P_{Actual}$) may be generally represented by the equation:

$$P_{Actual} = P_{Gross} - P_{Grade} - P_{Friction} \qquad (1)$$

where $P_{Gross}$ is gross amount of power used to propel the machine 10 along the work surface 102, $P_{Grade}$ is the change in power due to the change in elevation or grade of the machine, and $P_{Friction}$ is the power lost due to friction associated with the machine as it moves.

Under some operating conditions, when operating the machine 10 together with the vibration system 30, the accuracy of equation (1) may be reduced due to the affect of the vibration system on the work material 101. For example, in some situations, operation of the machine 10 with the vibration system 30 has resulted in reduction in the calculation of the actual drive power ($P_{Actual}$). As a result, equation (1) may provide a first result when the vibration system 30 is in operation and a second result for the same physical location and work material characteristics when the vibration system is off. As a result, a vibration compensation factor ($P_{Vibe}$) may be added to equation (1) to compensate for any changes due to the operation of the vibration system 30 as follows:

$$P_{Actual} = P_{Gross} - P_{Grade} - P_{Friction} + P_{Vibe} \qquad (2)$$

Figure 3:
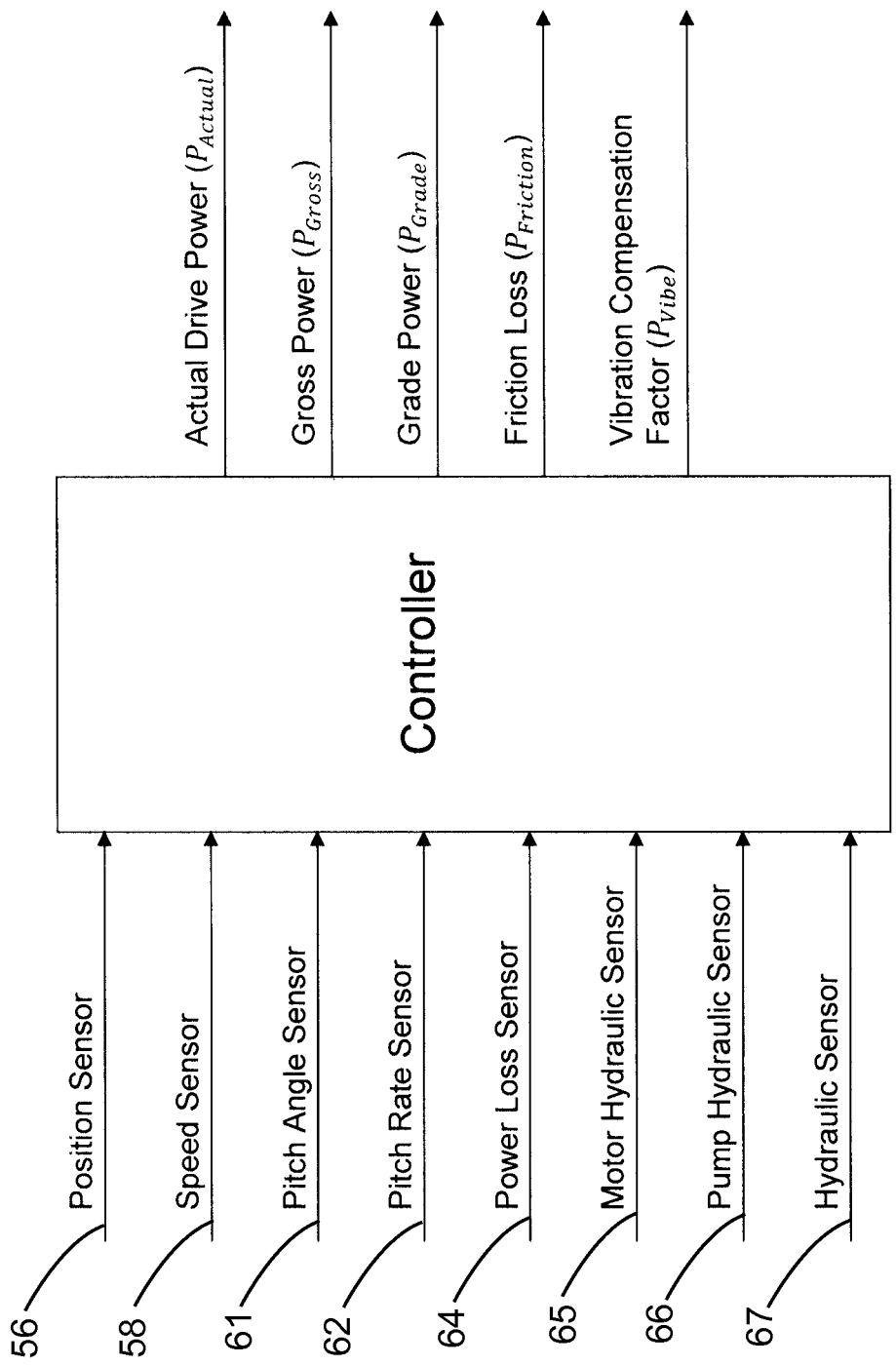
FIG. 3 illustrates a block diagram of state of compaction system in accordance with the disclosure.

As depicted in FIG. 3, the controller 51 receives information from various sensors and processes this information. Controller 41 may receive, at a first node a position signals from position sensor 56, speed signals from speed sensor 58 at a second node, and inclination signals from the pitch angle signal 61 at a third node. If a pitch rate sensor 62 is included, the controller 51 may receive pitch rate signals from the pitch rate sensor at a fourth node. At a fifth node, the controller 51 may receive signals from power loss sensor 64 indicative of power loss that occurs during a compacting operation. As described herein, the power loss sensor 64 may take any of various forms and examples of such sensors are indicated at the sixth through eighth nodes. Different power loss sensors would not typically be used together but are depicted in FIG. 3 as examples.

Controller 51 may generate various output signals based upon the operation of the state of compaction system 52. For example, at a first output node, the controller 51 may generate signals indicative of the gross amount of power ($P_{Gross}$) used to propel the machine 10 along the work surface 102. At a second output node, the controller 51 may generate signals indicative of the change in power ($P_{Grade}$) due to the change in elevation or grade of the machine. At a third node, the controller 51 may generate signals indicative of the power lost ($P_{Friction}$) due to friction associated with the machine 10 as it moves. At a fourth node, the controller 51 may generate signals indicative of a vibration compensation factor ($P_{Vibe}$) used compensate for any changes in the state of compaction system 52 due to the operation of the vibration system 30. At a fifth node, the controller 51 may use the gross amount of power ($P_{Gross}$) used, the change in power ($P_{Grade}$) due to the change in elevation, friction power loss ($P_{Friction}$) and the vibration compensation factor ($P_{Vibe}$) to generate signals indicative of the actual drive power ($P_{Actual}$) used for compaction and thus determine and display the state of compaction of the work material 101.

Figure 4:
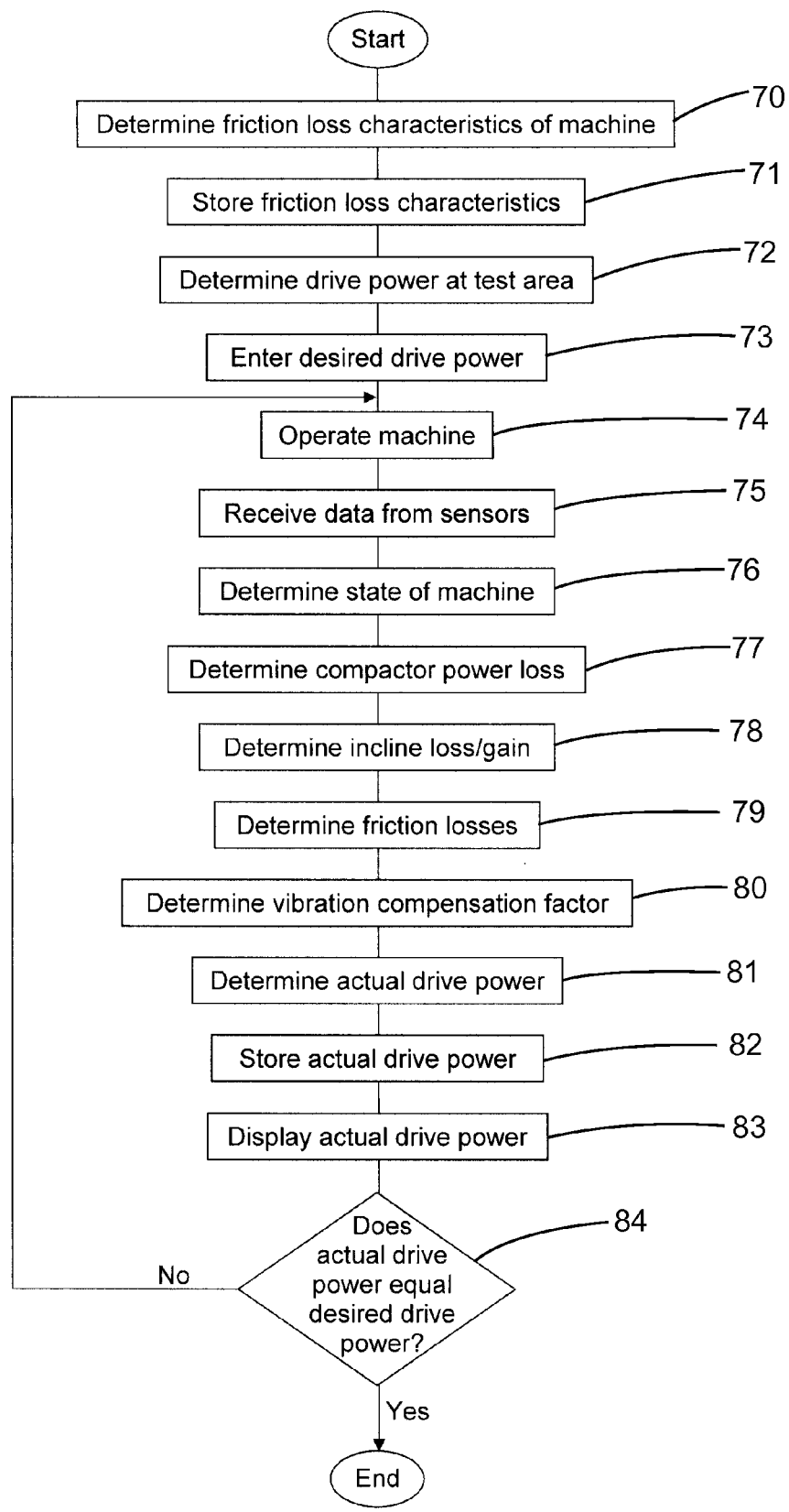
FIG. 4 illustrates a flowchart of a process for determining the state of compaction of a work surface during a compaction operation.

FIG. 4 depicts the operation of the state of compaction system 52 in conjunction with the operation of machine 10. At stage 70, the friction loss characteristics of the machine 10 may be determined. In doing so, the machine 10 is operated on a flat, hard calibration surface at various speeds without operating the vibration system 30 and the amount of power used when moving the machine at the different speeds is recorded. More specifically, the machine is positioned on a hard surface that does not deflect or compact under the weight of the machine as would occur with a compactable work material 101. In addition, the surface upon which the machine 10 is positioned is flat so that the machine is not going up or down a grade. As a result, the power required to move the machine along such a calibration surface does not include any energy used to compact the work material nor is there any energy loss or gain due to the machine moving up or down an incline. The power used as the machine 10 moves along the calibration surface thus accurately reflects only the friction losses of the machine required to move the machine such as the rolling resistance and other losses such as those caused by friction within the machine.

In one example, the friction losses may be determined by operating the machine 10 at a series of different speeds (e.g. 1 mph, 2 mph, 3 mph, 4 mph, etc.) while using the power loss measurement system 63 to determine the amount of power required to move the machine at each of those speeds. Friction losses may be extrapolated for values between the tested data points. If desired, the process may be repeated for different combinations of settings of the first pump 16 and the first motor 20 and the second pump 17 and the second motor 21. The calibration process may be performed at any desired location such as at a factory at which the machine is manufactured. The friction loss characteristics generated at stage 70 may be stored at stage 71 within controller 51.

If desired, rather than calibrate each machine 10, standard or generalized friction loss characteristics may be developed such as by averaging data from a plurality of machines and such standard friction loss characteristics may be stored within controller 51.

To begin operation at a work site 100, the machine operator or other personnel may determine a desired actual drive power ($P_{Actual}$) setting or reading for the work material 101. In one example, an operator may operate at stage 72 the machine 10 at a test area or physical location at which the state of compaction is known to meet a desired level of compaction based upon the measurement of engineering, industry and/or regulatory reporting requirements or standards. As the machine 10 moves over the area of known compaction, the state of compaction system 52 may display the actual drive power ($P_{Actual}$) on display 48. The operator may then enter at stage 73 the actual drive power ($P_{Actual}$) into controller 51 as a target or desired drive power for operating the machine 10 at the work site 100 or at a particular location at the work site. In other instances, the characteristics of the work material 101 may not be stored within the controller 51.

In another example, the machine 10 may be moved repeatedly over a particular location and the actual drive power ($P_{Actual}$) displayed on display 48. Once the actual drive power ($P_{Actual}$) becomes relatively constant, the value of the actual drive power may be used as the target or desired drive power.

At stage 74, the machine 10 may be moved to another location at the work site 100 and the compaction operation begun. As the machine 10 operates, the controller 51 may receive data from the various sensors at stage 75. At stage 76, the controller 51 may determine the state of the machine 10. More specifically, the controller 51 may determine the position of the machine 10 based upon position signals from the position sensing system 55 and determine the speed at which the machine is operating based upon speed signals from the drive speed sensing system 57. In addition, the controller 51 may also determine the pitch angle or inclination of the machine 10 based upon inclination signals from the inclination sensing system 60. If desired, the controller 51 may also determine the pressure of the hydraulic fluid within the vibration system 30 based upon signals from hydraulic sensor 67.

At stage 77, the controller 51 may determine the gross amount of power ($P_{Gross}$) used to propel the machine 10 along the work surface 102 as the machine 10 moves about the work site 100. In doing so, the controller 51 may utilize the power loss measurement system 63 as described above. In one example, the power loss measurement system 63 may measure the difference between the hydraulic pressure between the input and the output of each of the first motor 20 and the second motor 21. In another example, the power loss measurement system 63 may measure the difference between the hydraulic pressure between the input and the output of each of the first pump 16 and the second pump 17 together with an estimate of line losses between each pump and its respective motor. In still another embodiment, the power loss measurement system 63 may measure the difference between the input and the output of a torque converter used to drive the machine 10.

At stage 78, the inclination of the machine 10 as determined at stage 76 may be used to determine the change in power ($P_{Grade}$) due to the change in elevation or grade of the machine due to the incline on which the machine is operating. More specifically, the change in power ($P_{Grade}$) due to the incline may be determined as follows:

$$P_{Grade}=m*g*V*\sin(\alpha) \qquad (3)$$

where m is the mass of the machine, g is the force of gravity, V is the velocity of the machine and a is the angle of the machine relative to gravity.

Friction losses ($P_{Friction}$) caused by movement of the machine 10 may be determined at stage 79 based upon the friction loss data generated at stage 70. More specifically, the speed of the machine 10 determined at stage 77 may be used to determine the corresponding power required to overcome the friction losses ($P_{Friction}$) of the machine as it moves along the work surface 102.

In some instances, the power lost ($P_{Friction}$) due to friction associated with the machine 10 as it moves may not be specifically calculated as part of equation (1) or equation (2). In such case, the friction loss characteristics do not need to be stored within controller 51 nor the friction losses calculated. With such alternate procedure, as the desired actual drive power ($P_{Actual}$) is determined at stage 72, the operator or the machine 10 may note or store the speed of operation during such process. When operating the machine 10 at other locations at the work site 100, if the machine is moved at the same speed as the machine was operating while determining the desired actual drive power ($P_{Actual}$), the friction losses will be the same during the process of determining the desired actual drive power and determining the actual drive power at the work site. As such, the state of compaction system 52 will achieve consistent results provided that the speed of the machine 10 does not change while determining the actual drive power ($P_{Actual}$). In other words, since the power lost ($P_{Friction}$) due to friction is a function of the speed of the machine 10, the losses will be the same while determining the actual drive power ($P_{Actual}$) and while operating at the work site provided that the machine is operating at a consistent speed. In such case, the actual drive power ($P_{Actual}$) may be represented as follows:

$$P_{Actual}=P_{Gross}-P_{Grade}+P_{Vibe} \qquad (4)$$

A vibration compensation factor may be determined at stage 80. As stated above, the vibration compensation factor may be used to adjust the state of compaction system 52 to adjust for the use of vibration system 30. For example, under some operating conditions, use of the vibration system 30 may decrease the actual drive power ($P_{Actual}$) as determined by equation (1) and displayed on display 48. Accordingly, a vibration compensation factor ($P_{Vibe}$) may be used to create consistency between actual drive power ($P_{Actual}$) data regardless of whether the vibration system 30 is being operated.

In one example, a map of vibration compensation factor ($P_{Vibe}$) may be generated and stored within controller 51 by operating the machine 10 on a specific area or location of a work surface, both with and without the vibration system 30 operating. The actual drive power ($P_{Actual}$) may be recorded together with the frequency and amplitude of the vibration system 30. This process may be repeated for a plurality of different frequencies and amplitudes. Other factors such as the type of work material 101, the speed of machine 10, and the state of compaction of the work material may also affect the vibration compensation factor ($P_{Vibe}$) and may be stored as part of the data map of vibration compensation factors as well as for a plurality of It is contemplated that other factors may also affect the vibration compensation factor ($P_{Vibe}$). In operation, the controller 51 may use all of the factors used to generate the map of vibration compensation factors ($P_{Vibe}$) to determine the relevant vibration compensation factor at stage 80.

In an alternate embodiment, the vibration compensation factor ($P_{Vibe}$) may be determined based upon the pressure within the vibration system 30. More specifically, as the work material 101 is compacted and becomes stiffer, the pressure within the first vibration system hydraulic line 35 and the second vibration system hydraulic line 36 may increase. Hydraulic sensor 67 may be operatively associated with the vibration system 30 to determine the pressure of the relevant hydraulic line. It is believed that a correlation may be determined between the hydraulic pressure and the vibration compensation factor ($P_{Vibe}$). Accordingly, a data map vibration compensation factors ($P_{Vibe}$) corresponding to hydraulic pressure within the vibration system 30 may also be generated and stored within controller 51 in a manner similar to that described above. It is believed that it may be possible to use the change in pressure together with the frequency and amplitude of the vibration system 30 to further increase the accuracy of the actual drive power ($P_{Actual}$) calculation.

At stage 81, the controller may determine the actual drive power ($P_{Actual}$) according to equation (2) where the gross amount of power ($P_{Gross}$) is determined at stage 77, the change in power ($P_{Grade}$) due to the change in elevation or grade of the machine 10 is determined at stage 78, the power loss ($P_{Friction}$) due to friction associated with movement of the machine is determined at stage 79, and the vibration compensation factor ($P_{Vibe}$) is determined at stage 81.

It should be noted that while the change in power ($P_{Grade}$) due to the change in elevation is subtracted in equation (2), the change in power is either added or subtracted based upon whether the machine 10 is moving up or down a grade. Further, while the vibration compensation factor ($P_{Vibe}$) is indicated as being added to equation (1) to establish equation (2), there may be instances in which the vibration compensation factor is negative and is actually reduces the actual drive power ($P_{Actual}$) in equations (2).

The actual drive power ($P_{Actual}$) may be stored at stage 82 and displayed on display 48 at stage 83. At decision stage 84, the controller 51 may determine whether the actual drive power ($P_{Actual}$) is equal to the desired drive power. If the actual drive power ($P_{Actual}$) is not equal the desired drive power, the operator may continue to operate machine 10 at stage 74 and the process of stages 74-84 repeated. If the actual drive power ($P_{Actual}$) does equal the desired drive power at decision stage 84, the operator may move the machine 10 to a new location and begin a new compacting process, if desired.

INDUSTRIAL APPLICABILITY

The industrial applicability of the system described herein will be readily appreciated from the forgoing discussion. The foregoing discussion is applicable to machines 10 such as compactors that engage the work surface 102 above a work material 101 to compact the material to prepare it for a subsequent use or otherwise reduce its volume. Such system may be used at a construction site, a roadwork site, a mining site, a landfill, or any other area in which compaction of work material 101 is desired. Work material 101 may include any material such as asphalt, gravel, soil, sand, landfill trash, and other types of material.

When compacting a work material 101, it may be desirable to determine the state of compaction of the work material. The state of compaction system 52 is operative to utilize data from the sensors as well as the characteristics of the machine 10 to determine the state of compaction of the work material. The machine 10 may also utilize a vibration system 30 to increase the speed and/or extent of compaction of the work material 101. The use of the vibration system 30 affect the accuracy of the state of compaction system 52. Accordingly, the state of compaction system 52 may further use a vibration compensation factor ($P_{Vibe}$) to increase the accuracy of the system when using the vibration system 30. In this manner, the state of compaction system 52 may generate consistent data regardless of whether the vibration system 30 is being used. An electronic map of the work site 100 including the state of compaction may be generated and stored within controller 51 and/or at a remote location It will be appreciated that the foregoing description provides examples of the disclosed system and technique. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A system for determining a state of compaction of a work material during a compaction operation, comprising:

a roller associated with a machine and configured to engage and compact the work material, the roller including a vibration system;

a speed sensor associated with the machine for generating speed signals indicative of a speed of the machine;

a pitch angle sensor associated with the machine for generating inclination signals indicative of an inclination of the machine;

a power loss sensor associated with the machine for generating signals indicative of a power loss of the machine; and a controller configured to:
receive the speed signals from the speed sensor indicative of the speed of the machine;
determine the speed of the machine based upon the speed signals;
receive the inclination signals from the pitch angle sensor indicative of the inclination of the machine;
determine the inclination of the machine based upon the inclination signals;
determine an inclination power change based upon the inclination and the speed of the machine;
receive signals from the power loss sensor indicative of the power loss of the machine;
determine the power loss of the machine based upon the signals;
determine a vibration compensation factor based upon vibration characteristics of the vibration system; and
determine the state of compaction of the work material based upon the inclination power change, the power loss, and the vibration compensation factor.

2. The system of claim 1, wherein the controller is further configured to. store friction loss characteristics of the machine, determine a machine friction loss based upon the friction loss characteristics and the speed of the machine, and the state of compaction of the work material is further based upon the machine friction loss.

3. The system of claim 1, wherein the vibration compensation factor is based upon an amplitude of vibrations of the vibration system.

4. The system of claim 3, wherein the vibration compensation factor is based upon a frequency of vibrations of the vibration system.

5. The system of claim 4, wherein the vibration system includes a hydraulic drive system and the vibration compensation factor is based upon a pressure within the hydraulic drive system.

6. The system of claim 1, wherein the vibration compensation factor is based upon a frequency of vibrations of the vibration system.

7. The system of claim 1, wherein the vibration system includes a hydraulic drive system and the vibration compensation factor is based upon a pressure within the hydraulic drive system.

8. The system of claim 1, further including a position sensor associated with the machine for generating position signals indicative of a position of the machine, and the controller is further configured to determine the position of the machine based upon the position signals.

9. The system of claim 1, wherein the machine further includes a hydrostatic system having a pump operatively connected to a motor, and the motor is operatively connected to the roller.

10. The system of claim 9, wherein the controller is further configured to determine the power loss based upon a difference between an input and an output of the motor.

11. The system of claim 9, wherein the controller is further configured to determine the power loss based upon a difference between an input and an output of the pump.

12. The system of claim 1, wherein the machine further includes a hydrostatic system having a pump, and the controller is further configured to determine the power loss based upon a difference between an input and an output of the pump.

13. The system of claim 1, wherein the machine further includes a torque converter, and the controller is further configured to determine the power loss based upon a difference between an input and an output of the torque converter.

14. A machine comprising:
a prime mover;
a roller operatively connected to the prime mover and configured to engage and compact a work material, the roller including a vibration system;
a speed sensor associated with the machine for generating speed signals indicative of a speed of the machine;
a pitch angle sensor associated with the machine for generating inclination signals indicative of an inclination of the machine;
a power loss sensor associated with the machine for generating signals indicative of a power loss of the machine; and
a controller configured to:
receive the speed signals from the speed sensor indicative of the speed of the machine;
determine the speed of the machine based upon the speed signals;
receive the inclination signals from the pitch angle sensor indicative of the inclination of the machine;
determine the inclination of the machine based upon the inclination signals;
determine an inclination power change based upon the inclination and the speed of the machine;
receive signals from the power loss sensor indicative of the power loss of the machine;
determine the power loss of the machine based upon the signals;
determine a vibration compensation factor based upon vibration characteristics of the vibration system; and
determine the state of compaction of the work material based upon the inclination power change, the power loss, and the vibration compensation factor.

* * * * *